United States Patent

Sodickson et al.

[11] 3,937,614
[45] Feb. 10, 1976

[54] APPARATUS FOR MONITORING THE RATE OF A CHEMICAL REACTION

[75] Inventors: Lester A. Sodickson, Newton, Mass.; Franklin Lim, Richmond, Va.

[73] Assignee: Damon Corporation, Needham Heights, Mass.

[22] Filed: Aug. 28, 1974

[21] Appl. No.: 501,133

Related U.S. Application Data

[62] Division of Ser. No. 243,028, April 11, 1972, Pat. No. 3,844,717.

[52] U.S. Cl. ............... 23/253 R; 356/209; 250/461
[51] Int. Cl.[2] .................. G01N 21/38; G01N 21/48
[58] Field of Search ........... 23/253 R, 259; 250/458, 250/461, 484, 486, 552; 356/209

[56] References Cited
UNITED STATES PATENTS 3,245,306   4/1966   Potter et al. .................... 356/209
3,526,480   9/1970   Findl et al. ...................... 23/253 R Primary Examiner—Morris O. Wolk
Assistant Examiner—Timothy W. Hagan
Attorney, Agent, or Firm—Kenway & Jenney

[57] ABSTRACT

A press for compressing a liquid-bearing absorbent article to transfer a portion of the liquid materials to a contiguous article has two concentric pressure feet. One is an outer foot member that bears against the liquid-bearing article along the periphery of the pressure area, and the other is an inner, deformable and contoured foot member that applies pressure to the liquid-bearing article progressively along the pressure area. A photometer can be combined with the press to measure constituents or other properties of the liquid materials being transferred.

3 Claims, 7 Drawing Figures

APPARATUS FOR MONITORING THE RATE OF A CHEMICAL REACTION

This application is a division of pending application Ser. No. 243,028 filed Apr. 11, 1972 for "Press For Progressive Compression Of Liquid-Bearing Absorbent Article", now U.S. Pat. No. 3,844,717

BACKGROUND

This invention relates to a press for compressing an absorbent article to squeeze liquid materials from it. More particularly, the invention provides a press for transferring liquid and dissolved materials from one absorbent article to another layered with it. A particular feature of the invention is the provision of such a press that transfers the liquid materials with only minimal lateral spreading. This is desired to avoid loss of liquid materials in the first article and thereby to transfer the utmost volume of materials to the second article, and to concentrate the transferred materials in a confined region of the second article.

A press embodying the invention is particularly useful in connection with the analysis of a biological liquid sample to identify the concentration of one or more constituents. According to one technique for such an analysis as disclosed for example in U.S. Pat. Nos. 3,036,893; 3,216,804; 3,219,416; 3,260,413; 3,261,668; 3,331,665; 3,368,872; and 3,502,438; the sample is deposited on a first absorbent pad and then transferred to a second absorbent pad where, with the addition of chemical reagents, a reaction product is developed in an amount dependent on the concentration of a constituent in the original sample. The above-noted Natelson Patent No. 3,261,668 discloses an elementary flat-bed type of press for squeezing two layered pads together to enhance the transfer of liquid materials between them. However, this prior art press generally transfers only a relatively small portion of the liquid materials in one pad to the other pad; due, at least in part, to the fact that the press spreads the liquid. The press of the Natelson U.S. Pat. No. 3,331,665 operates with disks of the pad material and does not restrict spreading of liquid within the disks.

Also in the prior art are teachings regarding metalworking punch presses, such as is disclosed in Henricson U.S. Pat. No. 1,723,935, which strip the work piece from the punch after the punching operation. U.S. Pat. Nos. 2,160,676; 2,168,377; 2,265,331; 2,268,787; and 2,350,436 disclose further punch presses of this type.

SUMMARY OF THE INVENTION

A press embodying the invention and for the transfer of portions of a biological liquid sample and of selected dissolved constituents between two absorbent pads as noted above has two concentric pressure feet. An outer pressure foot engages the pads along an outer annular pressure surface, and generally with a resilient force. The inner pressure foot engages the pads initially along an annular area contiguously within the pressure surface of the outer foot, and then progressively inward along the entire pressure surface of the inner foot.

This pressing action that progresses inward from an outer peripheral ring to the center of the pressure area constrains liquid materials absorbed in the pads from spreading laterally outward. Instead, it urges the liquid materials in the initial liquid-bearing pad laterally inward to the center of the pressure area, as well as transversely into the other pad layered with it. Thus, the invention provides a press that transfers an utmost volume of liquid material from a selected localized area of one pad to the other, without significant loss due to laterally outward spreading of the liquid; and delivers the liquid materials to a confined area of the second pad. It should be noted that both pads can be cards, sheets or strips large enough to embrace many such confined areas.

Considered more broadly, the invention provides a press that subjects the article being pressed to a pressing force that is resilient and that has a tailored distribution such that the pressing force progresses across the pressure area.

In accordance with a further feature of the invention, a press of the above character compresses absorbent pads along an annular path and admits a pipette nozzle or other fluid conduit to deposit a liquid onto the compressed pads inside the annular area of compression. After removal of the nozzle, the press-while maintaining the annular liquid-constricting compression-compresses the pads throughout the area within the annular area of initial compression.

Further, a press according to the invention can be combined with a photometer in a manner that enables the photometer to monitor at least a surface of the pads being compressed. A novel fluorometer is a preferred form of photometer for this arrangement.

The invention comprises the features of construction, combinations of elements, and arrangement of parts exemplified in the constructions hereinafter set forth, and the scope of the invention is indicated in the claims.

BRIEF DESCRIPTION OF DRAWINGS

For a fuller understanding of the nature and objects of the invention, reference should be made to the following detailed description and the accompanying drawings, in which.

DESCRIPTION OF ILLUSTRATED EMBODIMENT

Figure 1:
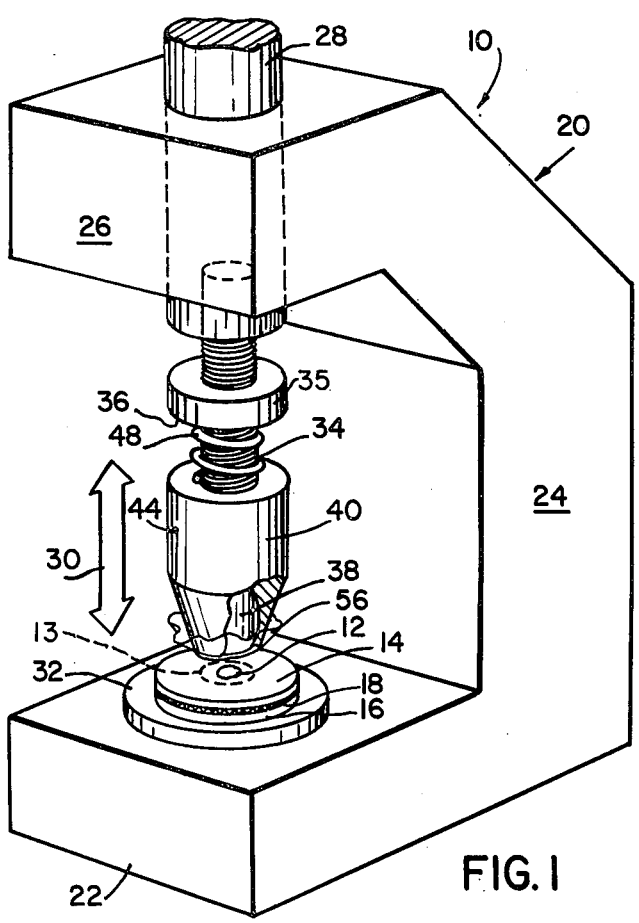
FIG. 1 is a perspective view, partly broken away, of a press embodying the invention and for the progressive compression of a liquid-bearing absorbent article to transfer a portion of the liquid and of materials dissolved in the liquid to a further absorbent article.
Figure 2:
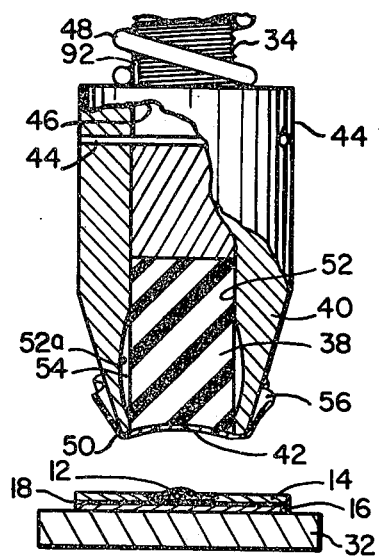
FIG. 2 is a fragmentary elevation view, partly broken away, showing details of the press of FIG. 1.

FIGS. 1 and 2 show a press 10 for squeezing a sample 12 of biological liquid and dissolved materials from a localized region 13 of an absorbent collection pad 14 to a selected localized site on an absorbent reaction pad 16. The sample is typically blood collected by blotting it into the collection pad 14 directly from a dermal puncture or with the aid of a transfer pipette or dropper. A portion of the sample is to be transferred to the reaction pad 16 for treatment there with one or more chemical reagents that produce, with the transferred sample constituents, a reaction product that is a measure the relative amount of a selected constituent in the original blood sample. Thus, the collection pad 14, which generally is separate from the reaction pad 16 during the collection of the sample, is shown layered above the reaction pad for the sample transfer operation which the press 10 carries out. A microporous sheet filter 18 is interposed between the two pads to block large molecules in the sample, e.g. blood proteins and hemiglobin, from being transferred to the reaction pad. After the transfer of sample to the reaction pad, the collection pad and filter typically are stripped from it and the reaction pad then subjected alone to the further constituent-analyzing processing.

With further reference to FIGS. 1 and 2, the press 10 has a base 20 forming a platen 22 affixed to an upstanding post 24 that carries a shaft support 26 spaced opposite the platen. The support slidably mounts a press shaft 28 for reciprocation relative to the platen as indicated with arrow 30. A conventional mechanism, not shown, operated either manually as with a lever arm or automatically by means of a motor drive, moves the shaft 28 selectively toward and away from the platen as the operator selects. The platen 22 can carry a pedestal 32 centered below the shaft 28 and on which the pads being pressed are placed, as indicated. At its lower end the shaft 28 threadably receives a threaded shank 34 of lesser diameter and which extends axially of the shaft. A disk 35 is threadably mounted on the shank to provide a shoulder 36 facing toward the platen 22.

Figure 3:
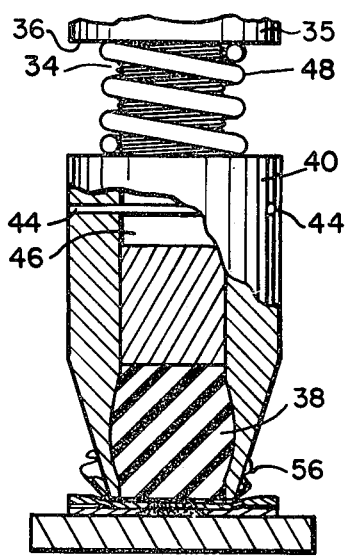
FIG. 3 is a view similar to FIG. 2 showing the press of FIG. 1 with the pressure feet in compressive engagement with the article being pressed.

The press shaft 28 carries two concentric foot members 38 and 40 on the lower end of the shank 34 for compressing work on the pedestal 32. The inner foot member 38 is a core or pluglike short rod of elastomeric material affixed as by adhesive or mechanical attachment on the end of the shank as an axial extension thereof. The inner foot member, illustrated as having a circular cross section and cylindrical side surface, has on the bottom end a concavely-domed pressure surface 42 that flattens, as shown in FIG. 3, upon axial compression of the foot member between the shaft and pedestal.

The outer foot member 40 is a collar of metal or like rigid material coaxially fitted on the end of the shank 34 over the inner foot member 38. The collar is slidable relative to the shank; a pin 44 is press fitted into the collar wall and seated in a slot 46 extending in the shank along the shaft axis to retain the collar on the shaft. A coil spring 48 is compressively seated between the top of the collar and the disk shoulder 36, encircling the shank 34, to urge the collar-like foot member forward along the shank toward the pedestal 32 for a distance limited by the axial length of the slot 46, as in FIG. 2.

The outer foot member 40 has an annular flat pressure surface 50 contiguously outside and encircling the domed pressure surface 42 of the inner foot member 38. The illustrated foot member 40 has a tapered thickness at its pressure end so that the radial width of the annular pressure surface 50 is narrow, which enhances the application of a large compressive pressure to the layered pads 14 and 16.

The outer foot member 40 has an inner surface 52 that is cylindrical along the length of the telescopic extension of that member over the shank 34, and at the extreme end of the member 40 adjacent its pressure surface 50, and along the end of the inner foot member connected to the shank for approximately the distance by which inner foot member decreases in length upon being fully pressed against the pads or other work on the pedestal.

The portion 52a of the surface 52 along the rest of the outer foot member is recessed outwardly. This recess forms a generally toroidal relief space 54 into which the inner foot member can bulge, substantially without restriction, when compressed as shown in FIG. 3. The surface portion 52a has a rounded contour and forms a smooth transition with the cylindrical sections of surface 52; for the purpose of allowing the two foot members to move, and the inner member to bulge, with minimal interference between them.

With the foregoing construction, when the shaft 28 moves down, toward the pads on the pedestal 32, the pressure surface 50 and the outermost edge of the domed pressure surface 42 engage the pads first. These surfaces compress the pads only along an annular area.

Continued descent of the shaft 28 presses the outer member down further with a resilient force as the spring 48 is increasingly compressed. It is considered preferable that the slot 46 extend along the shank for such a length that the pin 44 does not bottom against the slot upper end, which would then result in the outer member 40 being pressed with rigid force. Simultaneously, the inner foot member 38 is compressed axially. This causes it to bulge outwardly, into the recess 54, and gradually flattens the normally-domed pressure surface 42. Thus, the compressive force on the pads progresses inward from the annular area of initial compression until the entire area under the surfaces 50 and 42 is compressed.

This progressive compression of the pads 14 and 16 in accordance with the invention constrains the liquid sample 12 from spreading laterally outward. Instead, the sample is squeezed essentially straight down against the filter 18. This action transfers theoretically as much as one-half of the small-molecule portion of the sample to the portion of pad 16 lying directly under the pressure surface 42 of the inner foot member 38; in practice, typically twenty percent is transferred.

FIG. 3 shows the condition of the foot members of the press 10 when the shaft is at its lowermost position, i.e. at the position of full compression.

The shank 34 is threadably affixed to the shaft 28 to allow the shank to be threaded further into or out of the shaft and thereby adjust the pressure with which the foot member 38 engages pads on the press platen 22, and/or to allow operation with pads of different thicknesses. This adjustment of the shank 34 relative to the shaft 28 does not alter the compression of spring 48, which is done independently by threading the disk along the shank.

The provision of the relief space 54 between the two foot members 38 and 40 allows the inner foot member 38 to compressively deform in the manner shown and thereby enables the normally-domed pressure surface 42 to flatten progressively. In the absence of such a relief space 54, the two foot members seize upon each other and the desired compression of the pads 14 and 16 is generally not fully attained.

Figure 5:
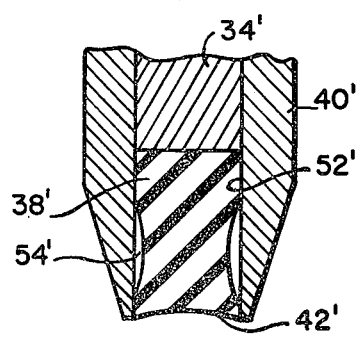
FIG. 5 is a view similar to FIG. 2 showing a modified construction for the press of FIG. 1.

It is considered preferable to form the relief space 54 with a geometry corresponding to the deformation of the inner foot member 38 when fully compressed, as shown in FIG. 3. Accordingly, the cross section of the relief space as shown in FIG. 2 is that of a shallow concavity. However, the relief space 54 can be provided with other shapes and can in fact be made larger than the laterally-outward bulging of the inner foot member when compressed. Moreover, the relief space 54 can, as shown in FIG. 5, be provided by recessing the outer diameter of the inner foot member rather than by recessing the inner surface of the outer foot member. Thus, FIG. 5, which shows elements corresponding to those in FIGS. 1 through 3 with the same reference numerals with an additional prime, has an outer foot member 40' with an inner surface 52' that is of right cylindrical shape throughout the length of the outer foot member. Further, the inner foot member 38' has, in addition to the normally-domed pressure surface 42', sidewalls forming an hourglass shape to provide the desired relief space 54' between the two foot members. It will now be apparent that further arrangements can be employed, including one in which both the outer surface of the inner member 38 and the inner surface of the outer member 40 are recessed to provide the relief space between them.

As further shown in FIGS. 1 through 3, the foot members 38 and 40 illustrated carry a barrier sheet 56 on their pressure surfaces and which is interposed between these pressure surfaces and the uppermost surface of the layered pads on the pedestal 32. The sheet 56 prevents the pressure surfaces from being contaminated by the sample 12 and other fluids or materials, e.g. chemical reagents, present with the collection pads 14 and/or 16. A fresh barrier sheet 56 is provided for each set of layered collection pads which the press processes; i.e. the sheet is discarded after a single use and replaced with a fresh one. This maintains the pressure surfaces free of contamination without requiring cleansing or a more-costly disposable element.

Figure 4:
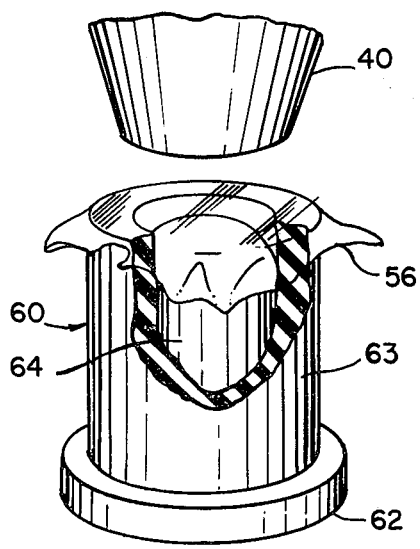
FIG. 4 is a perspective view, partly broken away, of an accessory device for use with the press of FIG. 1.

FIG. 4 shows a tool 60 for use in affixing the barrier sheet 56 to the foot members of the press 10. The tool has a rigid base 62 that carries an upstanding collar 63 of elastomeric material, and a core 64 within the collar bore. The core is of a harder material than the collar 63, polytetrafluoroethylene such as is marketed under the trade name "Teflon," or metal can be used for the core. Further, the core has a rounded upper surface conforming generally to the normally-domed shape of the inner pressure surface 42, whereas the upper surface of the collar 63 conforms to the outer annular pressure surface 50, although it may be wider than the latter surface.

In use, the fresh barrier sheet 56 is placed on the tool 60 as indicated and the tool seated on the press pedestal 32. The press shaft 28 is then lowered to compressively engage the pressure surfaces 50 and 42 with the tool collar 63 and core 64, respectively, with the barrier sheet interposed between. This compression of the barrier sheet 56 against the pressure surfaces conforms it to them as shown in FIG. 2, and causes the barrier sheet to self-adhere to the pressure surfaces, or to other outer surfaces of the foot member 40. A preferred material for the barrier sheet is a thin film of paraffin, as is marketed under the name Parafilm.

To illustrate the construction of a press in accordance with the invention, a press as shown in FIGS. 1 and 2 has an inner foot member 38 of synthetic rubber-like elastomeric material as sold under the name Tygon having a normal, i.e. uncompressed, length of 0.50 inch, an outer diameter of 0.375 inch, and a dome recess of approximately 0.50 inch maximum depth.

The relief space 54 extends for an axial length of 0.25 inch and has a maximum depth of approximately 0.01 inch.

Figure 6:
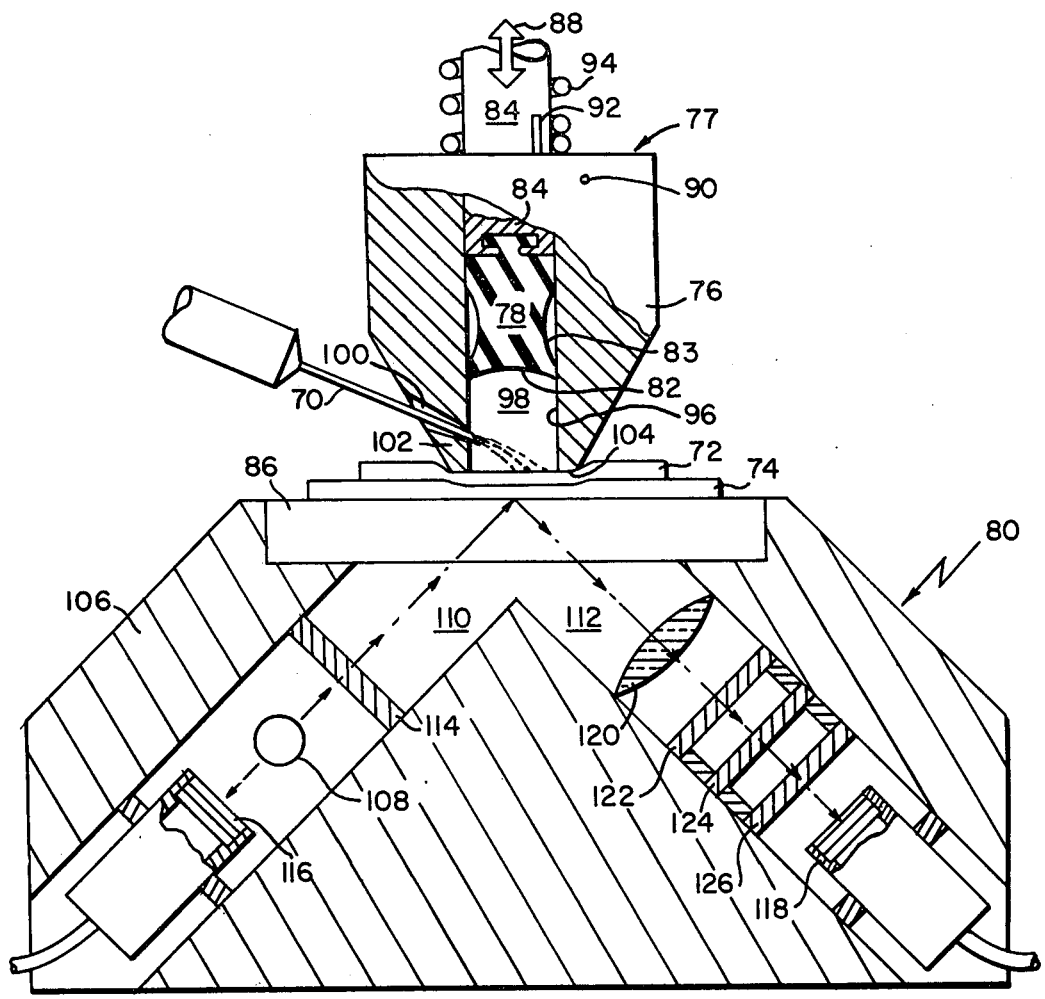
FIG. 6 is a fragmentary side elevation view, partly broken away, of a further embodiment of the invention incorporating a press and a photometric instrument for examining the article being pressed.

FIG. 6 shows another embodiment of the invention in which a pipette nozzle 70 can introduce a reagent to layered pads 72, 74 being compressed with a collarlike outer foot member 76 of a press 77, prior to being compressed with an inner foot member 78. Further, a photometer, illustrated as a fluorometer 80, is housed with the FIG. 6 press 77 to measure the reaction product produced in the reaction pad 74 while that pad is in the press.

More particularly, the press 77, generally similar to the press 10 of FIGS. 1 through 3, has a shaft shank 84 movable back and forth relative to a platen 86 as indicated by arrow 88. The inner foot member 78, illustrated as similar to the inner foot member 38' of FIG. 5, has a recessed pressure surface 82 and an hour-glass sidewall 83 having a cylindrical inner end section adjacent the shank, a cylindrical outer end section adjacent the pressure surface 82, and a thinned medial or waist section between the end sections and forming between the two foot members a recess of semi-lenticular cross-section. The foot member 78 is slidable within the bore of the outer member 76 with the sidewall end sections thereof in slidable engagement with the outer member bore and at least the outer end section forming a liquid-tight seal with the outer member 76.

As in the FIG. 1 press 10, the outer foot member 76 of FIG. 6 is affixed to shank 84 by means of a pin 90 seated in an axial slot 92 in the shank 92, and a compression spring 94 urges the outer foot member slidably forward relative to the shank in the direction toward the pedestal 86. The foot member 76 has an inner surface 96 similar to that described above with reference to FIG. 5, although a relieved inner surface such as is shown in FIG. 2 can be used instead.

As also illustrated, the inner foot member 78 has a locking tab on the inner end seated in a mating slot in the press shank 84 to secure the foot member to the shank. Further, the shank and outer foot member 76 are arranged such that the press has a normal configuration similar to that shown in FIG. 6, in which the compression spring 94 urges the outer foot member forward on the shank sufficiently to retract the inner foot member into the outer foot member to form a space 98 within the outer foot member for admitting the pipette nozzle 70.

In addition to this structure, outer foot member 76 is of sufficient axial length to contain the inner foot member 78 and the shank end to which it is secured when the foot member is retracted into the member 76 to form the space 98. Further, the outer foot member 76 has a passage 100 through the sidewall 102 thereof and spaced closely above the annular pressure surface 104. As FIG. 6 shows, this passage 100 admits the pipette nozzle 70, or another fluid conduit, for the injection of a fluid such as a diluent or reagent into the space 98 for deposition on the collection pad 72.

As FIG. 6 further illustrates, in a typical use of the press 77, the shaft is moved toward the platen to compress the pads 72, 74 slightly with the outer foot member 76, but without moving the inner foot member into the space 98, and is held in that position. The pipette nozzle 70 is then inserted through the passage 100 to enter the space 98 and the desired liquid is ejected onto the pad 72. The compressive engagement of the annular pressure surface 104 of the outer foot member against the pads 72, 74 precludes significant spreading of this liquid laterally outward beyond that pressure surface 104.

Figure 7:
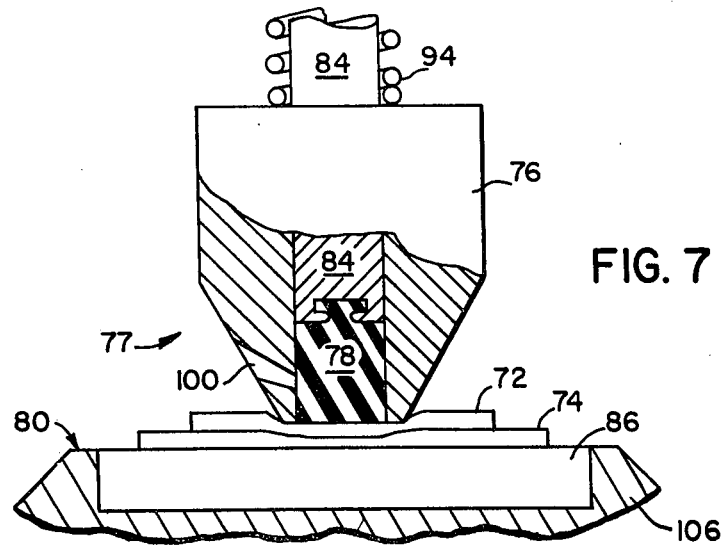
FIG. 7 is a fragmentary view of the press structure of FIG. 6 in the fully-compressed condition.

After the pipette nozzle is withdrawn from the space 98, the press shaft is moved further toward the platen to press the outer member further against the pad 72 and the slide the inner foot member 78 through the space 98 and compress it against the pad 72, as shown in FIG. 7. This compression transfers liquid materials from the pad 72 to the pad 74 through the intervening filter.

When the inner foot member is moved toward the platen beyond the opening of passage 100 through the surface 96 of the outer foot member, the outer end section thereof seals liquid from leaking out from within the outer foot member by way of the passage 100. The sealing engagement of the inner foot member to the bore surface 96 of the outer foot member increases as the shaft shank 84 increasingly compresses the inner foot member 78.

When the transfer operation is complete and the shaft shank is drawn away from the platen, spring 94 retracts the shank relative to the outer foot member, drawing the inner foot member to the retracted position of FIG. 6 where the space 98 is present.

With further reference to FIG. 6, the press base 106 also forms a housing for the fluorometer 80. The fluorometer illuminates the reaction pad 74 with radiation from a lamp 108 through the press platen 86, which is an optical window transparent to the incident exciting radiation of the lamp 108 and to the fluorescence which this radiation produces in the reaction product of interest in the reaction pad 74.

More particularly, the base 106 has a primary passage 110 and a secondary passage 112 therein; the passages are coplanar and are angled relative to each other with their central axes converging at the pad 74. The lamp 108 is mounted in the primary passage 110 in optical alignment through the optical window of the platen 86 with the section of the reaction pad under the inner foot member 78. A primary filter 114 is mounted in the primary passage interposed between the lamp 108 and the platen 86 to block unwanted radiation from illuminating the reaction pad. Further, a reference detector 116 for producing an electrical signal responsive to the intensity and modulation of the illumination from the lamp 108 also is mounted in the primary passage.

Although not required, the illustrated fluorometer secondary passage 112 is oriented along the angle at which incident radiation from lamp 108 reflects from the reaction pad 74. Thus, the illustrated fluorometer 80 has the secondary passage 112 aligned at the angle at which incident energy from lamp 108 reflects from the pad 74 surface which is contiguous with the optically-transparent platen 86. This geometry is preferred to provide equal-length optical paths, from lamp 108 to the detector 118 in the secondary passage 112, for illumination impinging on all points of the reaction pad 74 which are within the fluorometer field of view. The equal-length optical paths, in turn, result in high measuring accuracy and precision.

The secondary passage 112 mounts a fluorescence detector 118 and, in optical alignment between the detector 118 and the reaction pad 74, mounts a lens 120 which focuses the desired fluorescence onto the detector 118 and mounts secondary filters 122 and 124 and 126. These secondary filters together block reflected radiation from the lamp 108 and block fluorescence and other radiation above and below pass band of the fluorescence to be measured.

Further, the secondary filters are selected to be non-fluorescing, at least in the wavelength range of measurement, when excited with reflected illumination from the lamp 108 and with whatever fluorescence is present. Dielectric and metal film filter constructions are preferred to provide the filters 122, 124 and 126 with the desired degree of non-fluorescence. This provision of non-fluorescing secondary filters in accordance with the invention results in an increase in sensitivity and background rejection of the fluorometer 80 as contrasted to a fluorometer of similar construction except having glass or other secondary filters which are subject to producing fluorescence within the frequency range of measurement.

It will thus be seen that the objects set forth above, among those made apparent from the preceding description, are efficiently attained. Since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Optimum results are realized with the press described above when both pads on the press initially are dry except for the liquid sample on the collection pad. Further, it is preferred that the liquid sample initially be restricted to only the area below the inner pressure foot, so that the portion of the collection pad that is compressed by the outer pressure foot is dry at the time it is initially compressed. The initial dryness of the receiving, reaction pad is believed to enhance significantly the movement of liquid material from the collection pad through the intervening filter to the reaction pad.

Having described the invention, what is claimed as new and secured by Letters Patent is:

1. An instrument for analyzing liquid material carried in an absorbent article by monitoring a reactant formed from the liquid material in a reaction pad, said instrument comprising:
   A. a platen member of material transparent to selected radiation and having a first surface for supporting the pad during pressing,
   B. pressure means having a pressing surface disposed on a first side of said platen member for compressing the absorbent article between said pressing surface and said first surface of said platen member thereby to press the liquid material from the absorbent article to the reaction pad, and
   c. a fluorometer;
      1. disposed on the opposite, second side of said platen member,
      2. having an optical source for illuminating said first surface through said platen member with incident radiation, and
      3. having a fluorometric detector in optical alignment with said platen member first surface and said optical source for receiving, through said platen member, radiation emitted adjacent said first surface to response to said incident radiation, whereby analysis of the liquid material proceeds as reactant is developed on said reaction pad.

2. An instrument as defined in claim 1 in which said fluorometer detector is arranged to sense radiation directed along the same angle at which said incident radiation from said source reflects from said first surface.

3. An instrument as defined in claim 1 in which
A. said platen first member surface is planar,
B. said pressure means urges said pressing surface toward said platen member in a direction normal to said first surface,
C. said fluorometer source illuminates said first surface with incident radiation at a first angle relative to said surface, and
D. said fluorometer detector is aligned for sensing radiation directed from said first surface at said same first angle and in the direction in which said incident radiation reflects from said first surface.

* * * * *

UNITED STATES PATENT AND TRADEMARK OFFICE
CERTIFICATE OF CORRECTION

PATENT NO. : 3,937,614
DATED : February 10, 1976
INVENTOR(S) : Lester A. Sodickson and Franklin Lim It is certified that error appears in the above-identified patent and that said Letters Patent are hereby corrected as shown below:

Column 3, line 5, insert --of-- before "the relative".

Column 3, line 13, change "hemiglobin" to --hemoglobin--.

Column 7, line 7, before "slide" change "the" to --to--.

Column 8, line 68, after "surface", change "to" to --in--.

*Signed and Sealed this*

Thirtieth Day of November 1976

[SEAL]

Attest:

RUTH C. MASON
*Attesting Officer*

C. MARSHALL DANN
*Commissioner of Patents and Trademarks*